(12) United States Patent
Waldbaur et al.

(10) Patent No.: US 10,173,148 B2
(45) Date of Patent: Jan. 8, 2019

(54) PRE-HEATER ASSEMBLY WITH MODERATELY THERMALLY CONDUCTIVE CAPILLARY SURROUNDING

(71) Applicant: AGILENT TECHNOLOGIES, INC., Loveland, CO (US)

(72) Inventors: Ansgar Waldbaur, Karlsruhe (DE); Armin Steinke, Ettlingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 666 days.

(21) Appl. No.: 14/595,183

(22) Filed: Jan. 12, 2015

(65) Prior Publication Data

US 2015/0198382 A1 Jul. 16, 2015

(30) Foreign Application Priority Data

Jan. 13, 2014 (GB) .................... 1400519.3

(51) Int. Cl.
| | | |
|---|---|---|
| *F28D 15/04* | (2006.01) | |
| *F28F 23/00* | (2006.01) | |
| *B01D 15/16* | (2006.01) | |
| *F28F 13/00* | (2006.01) | |
| *F28F 21/06* | (2006.01) | |
| *F28F 1/00* | (2006.01) | |
| *G01N 30/30* | (2006.01) | |

(52) U.S. Cl.
CPC ............ *B01D 15/161* (2013.01); *F28F 1/00* (2013.01); *F28F 13/00* (2013.01); *F28F 21/06* (2013.01); *G01N 30/30* (2013.01); *F28F 2260/00* (2013.01); *G01N 2030/303* (2013.01); *G01N 2030/3046* (2013.01)

(58) Field of Classification Search
CPC ..... F28D 15/043; F28D 15/046; G01N 30/30; G01N 2030/303; G01N 2030/3046
See application file for complete search history.

(56) References Cited

U.S. PATENT DOCUMENTS

| | | | |
|---|---|---|---|
| 4,728,344 A | * | 3/1988 | Stacy ................... G01N 30/30 73/61.52 |
| 4,728,776 A | | 3/1988 | Vincent |
| 4,982,597 A | | 1/1991 | Berger |
| | | | (Continued) |

FOREIGN PATENT DOCUMENTS

| | | |
|---|---|---|
| EP | 309596 A1 | 4/1989 |
| EP | 0421595 A2 | 4/1991 |
| GB | 2432800 A | 6/2007 |

OTHER PUBLICATIONS

"Thermally Conductive Ceramics", Precision Ceramics, printed Aug. 31, 2017, pp. 1.*

(Continued)

*Primary Examiner* — Daniel S Larkin (57) ABSTRACT

A pre-heater assembly (90) for pre-heating a fluid, in particular in a fluid separation apparatus (10), wherein the pre-heater assembly (90) comprises a capillary (200) having a lumen and being configured for conducting the fluid, and a thermal coupling body (202) contacting at least part of the capillary (200), having a value of the thermal conductivity in a range between 8 W/(m K) and 100 W/(m K) and being arrangable so that heat generated by a heat source (80) is supplied to the capillary (200) via at least part of the thermal coupling body (202).

5 Claims, 5 Drawing Sheets

(56) References Cited

U.S. PATENT DOCUMENTS

| | | | | |
|---|---|---|---|---|
| 2003/0200795 A1* | 10/2003 | Gerner | .................. | G01N 30/30 |
| | | | | 73/61.52 |
| 2007/0181702 A1* | 8/2007 | Ziegler | ................. | G01N 30/30 |
| | | | | 237/19 |
| 2008/0145923 A1 | 6/2008 | Hahn et al. | | |
| 2009/0173146 A1* | 7/2009 | Pursch | .................. | G01N 30/30 |
| | | | | 73/61.52 |
| 2009/0211978 A1* | 8/2009 | Ognibene | .............. | B01D 15/12 |
| | | | | 210/656 |
| 2013/0139574 A1 | 6/2013 | Staats | | |
| 2013/0277350 A1 | 10/2013 | Arima | | |
| 2014/0150536 A1* | 6/2014 | Shreve | .................. | G01N 30/30 |
| | | | | 73/61.57 |
| 2015/0135861 A1* | 5/2015 | Cook | .................... | G01N 30/30 |
| | | | | 73/863.12 |

OTHER PUBLICATIONS

"Thermal—Thermal Conductivity—Characteristics of Fine Ceramics", Fine Ceramics World, printed Aug. 31, 2017, pp. 1-2.*
"Thermal Conductivity of Common Materials and Gases", The Engineering ToolBox, printed Sep. 2, 2017, pp. 1-4.*
"Thermally Conductive Polymers Delete the Heat", Machine Design, May 3, 2001, pp. 1-3.*
Lasance, C.J.M., "Thermal Conductivity of Filled Plastics", Electronics Cooling, No. 2, Technical Data, May 1, 2009, pp. 1-4.*
Sherman, L.M., "Plastics That Conduct Heat", Plastics Technology, Jun. 1, 2001, pp. 1-6.*
Search Report dated Jul. 15, 2014 in Application No. GB1400519.3.

\* cited by examiner

PRE-HEATER ASSEMBLY WITH MODERATELY THERMALLY CONDUCTIVE CAPILLARY SURROUNDING

The present application claims priority under 35 U.S.C § 119(e) from United Kingdom Patent Application No. 1400519.3 filed on Jan. 13, 2014 naming Ansgar Waldbaur, et al. as inventors. The entire disclosure of United Kingdom Patent Application No. 1400519.3 is specifically incorporated herein by reference.

BACKGROUND ART

The present invention relates to pre-heater assemblies for pre-heating a fluid, to a fluid separation apparatus, and to methods of manufacturing a pre-heater assembly for pre-heating a fluid.

In liquid chromatography, a fluid (such as a mixture between a fluidic sample and a mobile phase) may be pumped through conduits and a column comprising a material (stationary phase) which is capable of separating different components of the fluidic sample. Such a material, so-called beads which may comprise silica gel, may be filled into a column which may be connected to other elements (like a sampling unit, a flow cell, containers including sample and/or buffers) by conduits.

For operating a fluid separation apparatus, the fluid can be pre-heated by a pre-heater assembly located downstream of an injector for injecting the fluidic sample in the mobile phase and upstream of the column.

GB 2432800 discloses a chromatographic system and method which include a passive pre-heater assembly. A fluid mixture is supplied from an injector to the pre-heater assembly and then to a chromatographic column having an active heating source. The pre-heater assembly includes a convoluted tube with first and second ends and a fluid passage extending centrally therebetween, first and second end fittings attached respectively to the first and second ends of the convoluted tube, and a thermally conductive film attached to an outer surface of the convoluted tube. The first end fitting is adapted for fluidly connecting the first end of the convoluted tube to the injector and the second end fitting is adapted for fluidly connecting the second end of the convoluted tube to the chromatographic column. The thermally conductive film conveys heat from an active heating source of a chromatographic column to the convoluted tube when the pre-heater assembly is positioned adjacent to the active heating source. The central fluid passage in the convoluted tube has a series of bends which function to create a secondary fluid flow field that is substantially orthogonal to a primary flow field established when fluid is traversing the fluid passage in the tube.

However, when fluid is pre-heated in a conventional pre-heater assembly of a fluid separation apparatus, the heat transfer to the fluid is in many cases not satisfactory.

DISCLOSURE

It is an object of the invention to enable a fluid to be preheated efficiently.

According to an exemplary embodiment of the present invention, a pre-heater assembly for pre-heating a fluid, in particular in a fluid separation apparatus, is provided, wherein the pre-heater assembly comprises a capillary having a lumen and being configured for conducting the fluid, and a thermal coupling body contacting (in particular surrounding) at least part of the capillary, having a value of thermal conductivity in a range between approximately 8 W/(m K) and approximately 100 W/(m K) and being arrangable so that heat generated by a heat source is supplied to the capillary via at least part of the thermal coupling body.

According to an exemplary embodiment of the present invention, a pre-heater assembly for pre-heating a fluid, in particular in a fluid separation apparatus, is provided, wherein the pre-heater assembly comprises a capillary having a lumen and being configured for conducting the fluid, and a thermal coupling body contacting (in particular surrounding) at least part of the capillary, made of plastic (such as a polymer material) and being arrangable so that heat generated by a heat source is supplied to the capillary via at least part of the thermal coupling body.

According to another exemplary embodiment, a fluid separation apparatus for separating a fluidic sample into a plurality of fractions is provided, wherein the apparatus comprises a fluid drive unit configured for driving a fluid comprising a mobile phase and the fluidic sample in the mobile phase, a separation unit configured for separating the fluidic sample into the plurality of fractions, and a pre-heater assembly having the above mentioned features for pre-heating the fluid upstream of the separation unit.

According to still another exemplary embodiment, a method of manufacturing a pre-heater assembly for pre-heating a fluid, in particular for a fluid separation apparatus, is provided, wherein the method comprises providing a capillary having a lumen and being configured for conducting the fluid, forming a thermal coupling body of a material having a value of thermal conductivity in a range between approximately 8 W/(m K) and approximately 100 W/(m K), contacting at least part of the capillary to the thermal coupling body, and arranging the thermal coupling body so that heat generated by a heat source is supplied to the capillary via at least part of the thermal coupling body.

According to still another exemplary embodiment, a method of manufacturing a pre-heater assembly for pre-heating a fluid, in particular for a fluid separation apparatus, is provided, wherein the method comprises providing a capillary having a lumen and being configured for conducting the fluid, forming a thermal coupling body of a plastic material, contacting at least part of the capillary to the thermal coupling body, and arranging the thermal coupling body so that heat generated by a heat source is supplied to the capillary via at least part of the thermal coupling body.

According to an exemplary embodiment, a capillary for conducting a fluid is surrounded by a thermal coupling body having a comparatively (i.e. in comparison to conventionally used thermal coupling bodies of aluminum or the like) small thermal conductivity, but still showing a thermal conductivity which is by far better than that of thermal insulators. With such a moderately thermally conductive thermal coupling body, it is surprisingly possible to pre-heat the flowing fluid in a particularly efficient way making use of a heat transfer via the thermal coupling body. This intended pre-heating can be achieved by heat conduction between a heat source and an external exposed surface of the thermal coupling body. Surprisingly, the implementation of a thermal coupling body with an only moderate thermal conductivity shows an improved pre-heating performance as compared to a highly thermally conductive material such as aluminum. Without wishing to be bound to a specific theory, it is presently believed that the reason for this behavior is that apart from the flow of thermal energy from the heat source through the thermal coupling body to the fluid within the capillary there is another—parasitic—heat flow path which has to be taken into account as well. This parasitic heat flow path is due to heat conduction between different sections of the fluid in the capillary and via adjacent material of the thermal coupling body. The fluid is heated while traversing the pre-heater assembly. However, hotter fluid sections have the tendency to heat cooler fluid sections and will therefore lose temperature to thereby equilibrate the spatial temperature distribution within the flowing fluid. This occurs by heat conduction from hotter downstream sections of the fluid towards cooler upstream sections of the fluid. This heat flow is parasitic since it tends to foil the desired heat flow from the heat source via the thermal coupling body through the capillary into the fluid. It has turned out that by using a material with a moderate thermal conductivity for the thermal coupling body, the efficiency of the desired heat flow might be slightly reduced, but the parasitic heat flow is even more efficiently suppressed. It has turned out that the net effect of the use of a material for the thermal coupling body with a thermal conductivity between about 8 W/(m K) and about 100 W/(m K) such as the use of an appropriate plastic-based thermal coupling body improves the overall performance of the pre-heater assembly because the dramatic suppression of the parasitic heat flow overcompensates the only slight deterioration of the desired heat flow. Moreover, using a plastic thermal coupling body allows for a simple manufacturability (for instance by molding) and an embedding of the capillary by an encapsulant forming the thermal coupling body, further promoting the thermal coupling within the pre-heater assembly.

In the following, further embodiments of the pre-heater assemblies, the fluid separation apparatus, and the methods will be explained.

In an embodiment, the capillary is a wound capillary. By winding the capillary (for instance exclusively) within the thermal coupling body, the effective length of the capillary through which the fluid flows while being pre-heated is increased. For instance, the wound capillary may have a helical shape, may have a folded shape, may have a meandrical shape, or may have a shape corresponding to a combination of two or more of the mentioned or other wounded shapes. A spirally shaped or helically wound capillary has the particular advantage of a very low dispersion. This is advantageous for the accuracy of a chromatographic analysis.

In an embodiment, the pre-heater assembly comprises a carrier around which the capillary is wound. Thus, the carrier may function as a mechanical support of the wound capillary keeping the capillary in position while the thermal coupling body is formed, and also contributes to the heat transfer properties of the pre-heater assembly. It is also possible that a capillary-accommodating groove is formed around the carrier (which may be shaped like a rod) along which the capillary may be wound around the carrier to precisely define a guided trajectory of the capillary within the pre-heater assembly (in particular a heat exchanger).

Correspondingly, the method may further comprise winding the capillary around such a carrier before forming the thermal coupling body to surround at least part of the wound capillary. The carrier and the thermal coupling body may be made of the same material (for instance also having a thermal conductivity between about 8 W/(m K) and about 100 W/(m K) such as an appropriate plastic) or of different materials (for instance steel).

Alternatively and preferably, the method further comprises winding the capillary isolatedly (for instance without a carrier) before forming the thermal coupling body which then at least partially surrounds the wound capillary. In such an embodiment, the entire interior and exterior of the capillary may be encapsulated by the thermal coupling body, for instance by molding or casting. A wound capillary encapsulated without a carrier can be made from a stiff but bendable material to keep the capillary in place and position after winding and before encapsulating.

In an embodiment, material of the thermal coupling body between adjacent windings of the capillary is thicker than material of the thermal coupling body between an exterior part of the capillary and an external surface of the pre-heater assembly. Then, the heat has to traverse only a shorter path in the desired radial direction (from heat source to capillary) as compared to the parasitic axial direction (from already pre-heated fluid to not yet pre-heated fluid). This improves the desired thermal coupling between the heat source and the fluid in the capillary, while weakening the parasitic thermal coupling in the axial direction.

In an embodiment, the thermal coupling body is made of a non-metallic material, in particular of plastic, more particularly of plastic filled with thermally conductive particles. This is particularly appropriate, because a thermal coupling body of plastic may be formed in a cheap way by molding. Configuring the mold compound as a mixture of a plastic matrix with thermally conductive filler particles allows to adjust the value of the (intentionally only) moderate thermal conductivity of the thermal coupling body.

In an embodiment, the thermal coupling body has a value of thermal conductivity in a range between approximately 10 W/(m K) and approximately 60 W/(m K), in particular in a range between approximately 10 W/(m K) and approximately 30 W/(m K). A value of thermal conductivity of 20 W/(m K) has turned out to be highly appropriate and can be achieved by selecting an appropriate plastic composition, if desired filled with a thermal conduction boosting filler.

In an embodiment, the thermal coupling body is arranged so that the heat from the heat source is supplied to the fluid along a heat flow direction which is substantially perpendicular to an effective fluid flow direction through the capillary. In this context, the term "effective fluid flow direction through the capillary" may denote a direction defined by connecting a position of the capillary at a fluidic inlet of the pre-heater assembly with a position of the capillary at a fluidic outlet of the pre-heater assembly. This direction may hence extend axially along the pre-heater assembly, whereas the heat transfer from the heat source occurs radially. In other words, the effective fluid flow direction may relate to a flow direction along which the fluid effectively flows from an intersection between an upstream flange face of the thermal coupling body and the capillary to an intersection between a downstream flange face of the thermal coupling body and the capillary.

In an embodiment, the thermal coupling body is arranged so as to suppress a heat flow along a heat flow direction which is substantially antiparallel to (i.e. is oriented opposing to) the effective fluid flow direction through the capillary. By limiting the parasitic heat flow from the hotter fluid to the cooler fluid as a result of the only moderate thermal conductivity of the thermal coupling body undesired heat equilibration can be efficiently suppressed.

In an embodiment, the pre-heater assembly comprises a fluid inlet interface fluidically coupled to one end of the capillary and/or comprises a fluid outlet interface fluidically coupled to an opposing other end of the capillary. The fluid inlet interface and/or the fluid outlet interface may be configured to be fluidically connected to a fluidic member to be connected, in particular via a fitting at the respective interface. More specifically, the pre-heater assembly may comprise a fluid inlet interface at an intersection between an upstream flange face of the thermal coupling body and the capillary, and/or a fluid outlet interface at an intersection between a downstream flange face of the thermal coupling body and the capillary. The fluid inlet interface and/or the fluid outlet interface may be configured to be selectively fluidically connectable to or fluidically disconnectable from a fluidic member (such as a component of the fluid separation apparatus). This may be accomplished via a fitting at the respective fluid inlet interface or fluid outlet interface. A female fitting is particularly advantageous in view of its high robustness. However, also a fitting free configuration at least on one end of the pre-heater assembly may be advantageous in order to achieve a very low dispersion, resulting in a highly accurate chromatographic analysis.

In an embodiment, the pre-heater assembly is substantially shaped as a regular prism with a triangular base surface, in particular with an equilateral triangular base surface (i.e. a triangle having three angles of 60° each). In this context, the term "prism" may denote a body with an n-sided polygonal base surface (n may for instance be 3, 4 5, or 6), a translated copy of the n-sided polygonal base surface in another plane as the first n-sided polygonal base surface, and n other surfaces configured as rectangles joining corresponding sides of the two base surfaces. Geometrically, all cross-sections parallel to the base surfaces are the same. Such a base surface may be a flange surface. More precisely, two opposing flange faces may be arranged as base surfaces at two opposing ends of the prism-shaped pre-heater assembly. The capillary may exit the thermal coupling body at each of the two bases surfaces. With such a configuration, two of three mutually slanted surfaces of the pre-heater assembly extending perpendicular to the base surfaces can be brought in direct physical contact with walls delimiting a correspondingly shaped recess in a mounting board for a pronounced thermal heat transfer from the heat source via the board to the thermal coupling body of the pre-heater assembly.

Although a prism with triangular base surfaces corresponding to three planar side faces is particularly advantageous in view of its very good guiding and fitting characteristics when being mounted with form closure in an inverse shaped groove (V-shaped groove) of the mounting board and provides remarkably good thermal coupling characteristics with the board while showing only small heat losses at an exposed outer surface, other shapes of the thermal coupling body are possible as well (for instance circular, semi-circular, or rectangular base surfaces).

In an embodiment, substantially an entire external heat transfer surface of the pre-heater assembly is constituted by the thermal coupling body. In other words, it is possible that the exposed outer surface of the thermal coupling body forms the entire heat coupling surface of the pre-heater assembly, in particular the entire outer surface of the pre-heater assembly (in particular with the only exception of the fluidic interfaces to the capillary at an inlet and an outlet of the pre-heater assembly).

In an embodiment, the capillary is at least partially (in particular fully circumferentially) embedded within the thermal coupling body. In other words, the (for instance wound) capillary may be encapsulated (for instance overmolded) by the material of the thermal coupling body. This provides for a proper heat transfer and an easy manufacturability.

In an embodiment, the thermal coupling body is constituted by a molding compound or a casting compound. Hence, the thermal coupling body is formed by overmolding or overcasting the capillary. The molding compound can be of a plastic or a ceramic material, for instance. The casting compound may be a moderately thermally conductive metal (such as steel), for instance. Both overmolding and overcasting ensures an intimate heat coupling between capillary and thermal coupling body.

In an embodiment, the capillary is made of steel, or of plastic material surrounded by steel. A steel capillary provides for a proper thermal transfer between an exterior and an interior of the capillary. The provision of plastic material delimiting the lumen is a proper selection in case that a chemical and/or biological inertness is desired (for instance when biological fluids have to be transported through the lumen).

In an embodiment, the pre-heater assembly is configured as a pre-column heat exchanger for a liquid chromatography apparatus. In such an embodiment, the fluid may be pre-heated by heat conduction in the pre-heater assembly and may be later further heated by heat convection in a separation unit. Both pre-heater assembly and separation unit may be heated by thermal energy of one and the same heat source, or by different heat sources.

In an embodiment, the fluid separation apparatus comprises an injector for injecting the fluidic sample into the mobile phase, wherein the injector is arranged upstream of the pre-heater assembly. In other words, the pre-heater assembly may be arranged downstream of the injector and upstream of the separation unit. In this section of a fluid separation apparatus, pre-heating and additional heating of the fluid is advantageous for conditioning the latter for proper separation of the fluid in its fractions.

In an embodiment, the fluid separation apparatus comprises the heat source configured for generating heat for heating the separation unit and for pre-heating the fluid in the pre-heater assembly via at least part of the thermal coupling body when the fluid is conducted through the lumen of the capillary. Such a heat source may be a Peltier heater.

In an embodiment, the fluid separation apparatus comprises a board being thermally coupled with the heat source, and having at least one accommodation recess configured for receiving the pre-heater assembly, in particular with a form closure. In an embodiment, the board comprises a plurality of grooves as the accommodation recesses. The thermal coupling of the pre-heater assembly arranged with full physical contact in such a groove is excellent.

In an embodiment, the board comprises or consists of a highly thermally conductive material (for instance having a value of thermal conductivity of at least 200 W/(m·K)), in particular aluminum or copper. The board may be integrally formed of such a highly thermally conductive material, which only needs to be provided with the accommodation recesses for accommodating the pre-heater assembly. The board may, on the other hand, be directly coupled with a heat source, so that the heat can flow from the heat source, via the board, by heat conduction to and through the thermal coupling body, through the capillary and towards the fluid.

The separation unit may be filled with a separating material. Such a separating material which may also be denoted as a stationary phase may be any material which allows an adjustable degree of interaction with a sample fluid so as to be capable of separating different components of such a sample fluid. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the separation unit may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The separation unit may be a chromatographic column for separating components of the fluidic sample. Therefore, exemplary embodiments may be particularly implemented in the context of a liquid chromatography apparatus.

The fluid separation system may be configured to conduct a liquid mobile phase through the separation unit. As an alternative to a liquid mobile phase, a gaseous mobile phase or a mobile phase including solid particles may be processed using the fluid separation system. Also materials being mixtures of different phases (solid, liquid, gaseous) may be processed using exemplary embodiments. The fluid separation system may be configured to conduct the mobile phase through the system with a high pressure, particularly of at least 600 bar, more particularly of at least 1200 bar.

The fluid separation system may be configured as a microfluidic device. The term "microfluidic device" may particularly denote a fluid separation system as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector of a liquid chromatography apparatus which sample injector may take up a sample fluid from a fluid container and may inject such a sample fluid in a conduit for supply to a separation column. During this procedure, the sample fluid may be compressed from, for instance, normal pressure to a higher pressure of, for instance several hundred bars or even 1000 bar and more. An autosampler may automatically inject a sample fluid from the vial into a sample loop. A tip or needle of the autosampler may dip into a fluid container, may suck fluid into the capillary and may then drive back into a seat to then, for instance via a switchable fluidic valve, inject the sample fluid towards a sample separation section of the liquid chromatography apparatus.

The fluid separation system may be configured to analyze at least one physical, chemical and/or biological parameter of at least one component of the sample fluid in the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluid separation system may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluid separation system may be a High Performance Liquid Chromatography (HPLC) device by which different fractions of analyte may be separated, examined and analyzed.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.aqilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable. One embodiment comprises two pumping apparatuses coupled either in a serial (e.g. as disclosed in EP 309596 AD or parallel manner.

The mobile phase (or eluent) can be either a pure solvent or a mixture of different solvents. It can be chosen e.g., to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a BRIEF supercritical fluid (as e.g. used in supercritical fluid chromatography—SFC—as disclosed e.g. in U.S. Pat. No. 4,982,597 A).

DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

The illustration in the drawing is schematic.

Before, referring to the figures, exemplary embodiments will be explained in further detail, some basic considerations will be explained based on which exemplary embodiments have been developed.

An exemplary embodiment of the invention provides for an integration of an arbitrarily bent/shaped capillary into an arbitrary outer shape in form of a thermal coupling body. More specifically, exemplary embodiments of the invention provide robust pre-heater assemblies as heat exchangers which are also very user convenient, as it may be sufficient that the user handles only a single monolithic part (i.e. the pre-heater assembly) which may also be provided with integrated fittings. As the shape of a capillary in the inside can be freely chosen, fluid properties can be optimized. As the outer shape defined by the thermal coupling body (which may also be denoted as a jacket) can be freely chosen, heat transfer properties as well as space utilization in device housings can be optimized. Truly three-dimensional shapes are possible.

According to an exemplary embodiment, a manufacturing method is provided which is capable to greatly facilitate integration of an arbitrarily (for instance user defined) bent/shaped capillary into an arbitrary outer shape in form of the thermal coupling body to improve properties of the carried liquid (like, for instance, dispersion) while also improving heat transfer at reduced cost. A core or carrier of the pre-heater assembly may be made of appropriate material (as, for instance, heat conductive plastics or metal). This carrier serves as guide to bend a capillary in desired shape and keep it in place. Fittings can be added, if necessary. In particular, the provision of a female fitting on a front end (but not limited to a front end) is possible. Female fittings may lead to a very robust design, as no parts are likely to be broken when being handled by the user. The thermal coupling body as a jacket/enclosure may be built around the carrier. Exemplary embodiments of corresponding manufacturing procedures include (but are not limited to) investment casting, injection molding, compression of one or multiple parts around the core.

Figure 1:
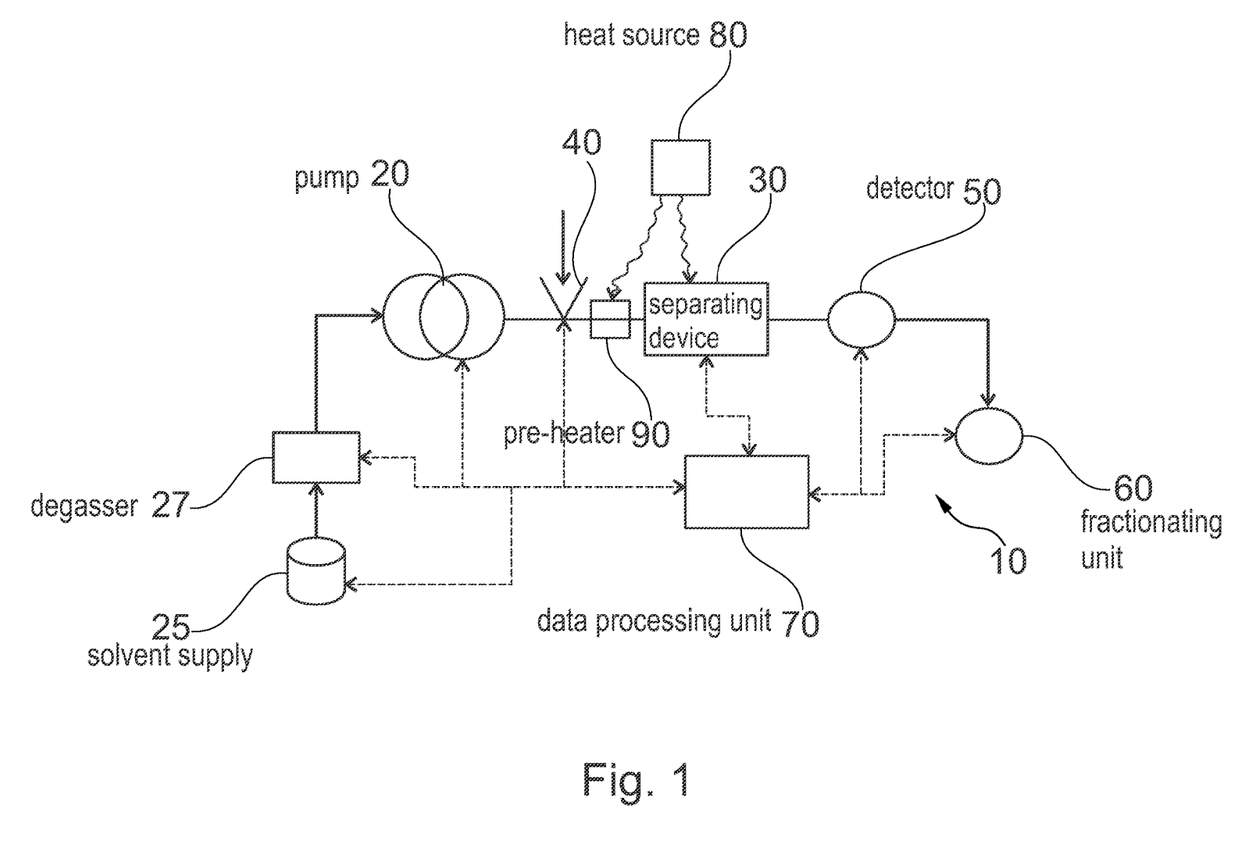
FIG. 1 shows a liquid separation device in accordance with embodiments of the present invention, particularly used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied overtime, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) which provides data back.

FIG. 1 also shows a heat source 80 for generating thermal energy, i.e. heat, and can for instance be embodied as a Peltier heater or an ohmic heater. The heat source 80, in the shown embodiment, fulfils two tasks. Firstly, the heat source 80 heats a pre-heater assembly 90 according to an exemplary embodiment by heat conduction, wherein the pre-heater assembly 90, in turn, pre-heats fluid downstream of the injector 40 and upstream of the separating device 30. Secondly, the heat source 80 heats the separating device 30 by heat convection, wherein the separating device 30, in turn, heats the fluid within the separating device 30.

Figure 2:
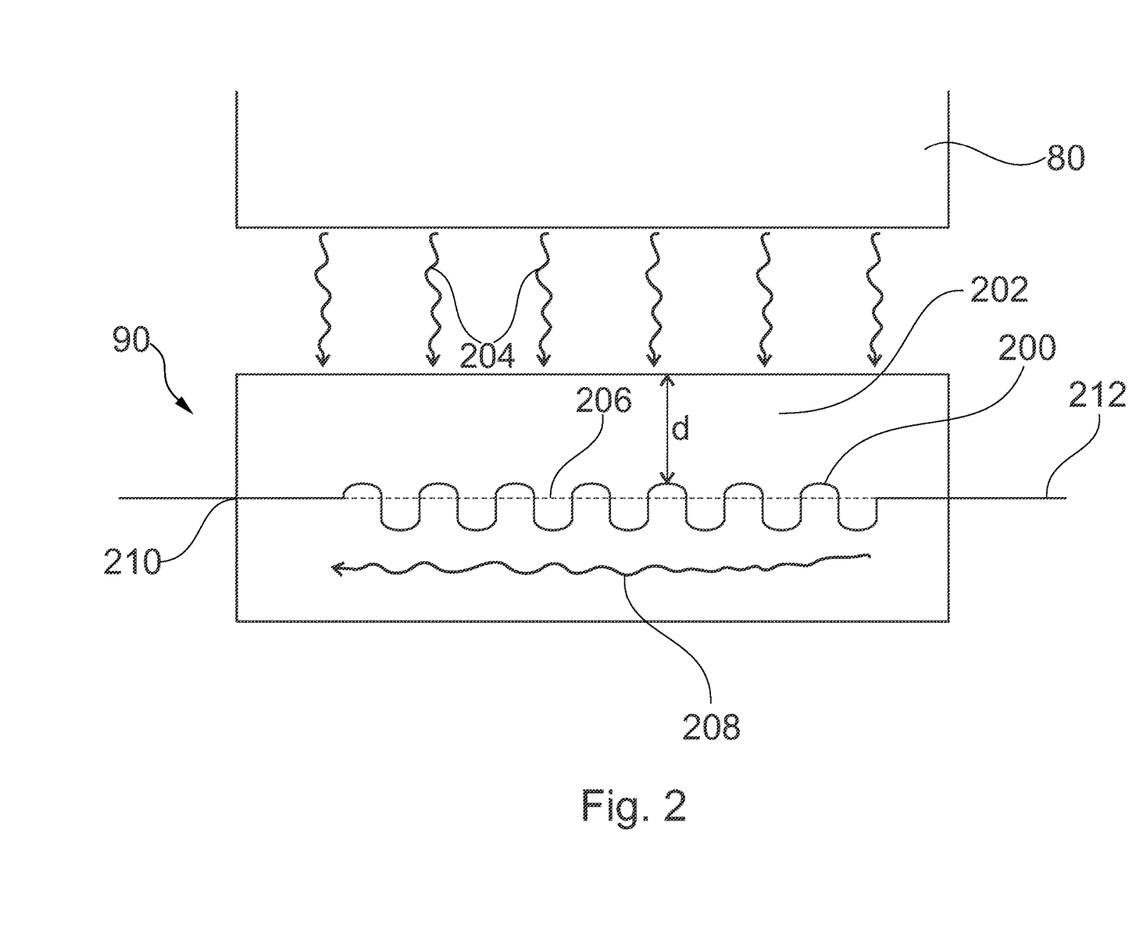
FIG. 2 is a schematic illustration of a pre-heater assembly according to an exemplary embodiment being supplied by thermal energy from a heat source.

FIG. 2 is a schematic illustration of the pre-heater assembly 90 according to an exemplary embodiment being supplied by thermal energy from the heat source 80.

The pre-heater assembly 90 is configured for pre-heating a liquid (for instance a mixture between a mobile phase in form of one or more solvents and a fluidic sample to be separated by the fluid separation apparatus 10), The pre-heater assembly 90 comprises a (for instance helically or meandrically) wound capillary 200 having a lumen. The capillary 200 can be made of steel or, for instance if the liquid to be conducted is a biological fluid, can be made of steel with an interior layer of biocompatible plastic such as PEEK, PTFE, etc. The capillary 200 is configured for conducting the liquid when it is driven by a fluid drive unit such as pump 20. The capillary 200 may be formed with such a small inner diameter that the flow of the liquid within the lumen is laminar. The capillary 200 is monolithically embedded and fully surrounded by a thermal coupling body 202 configured as a plastic molding compound (optionally with filler particles to adjust the value of thermal conductivity of the thermal coupling body 202) contacting the full circumferential surface of the capillary 200. When the plastic material of the thermal coupling body 202 is mixed with thermally conductive filling particles, the resulting thermal coupling body 202 can be adjusted to have a value of thermal conductivity of approximately 20 W/(m K). This is a moderate value being higher than that of many thermally insulating plastic materials and being lower than that of conventional thermally conductive materials such as copper or aluminum (conventionally used thermally conductive materials may have a value of thermal conductivity of more than 200 W/(m K)). The thermal coupling body 202 forms an outer surface of the pre-heater assembly 90.

As can be taken from the schematic drawing in FIG. 2, the thermal coupling body 202 is arranged so that heat generated by the heat source 80 (such as a Peltier heater) is supplied to the capillary 200 (and from there to the conducted liquid) via the thermal coupling body 202. Preferably but not necessarily, the heat transfer mechanism from the heat source 80 to the capillary 200 is heat conduction. FIG. 2 also shows an effective fluid flow direction 206 which is defined by a connection line between a fluid inlet interface 210 and a fluid outlet interface 212 of the pre-heater assembly 90, i.e. positions where the capillary 200 intersects with the thermal coupling body 202. Although the liquid traversing the pre-heater assembly 90 follows the wound trajectory of the capillary 200 embedded by the material of the thermal coupling body 202, the liquid effectively flows along the effective fluid flow direction 206. The heat transfer from the heat source 80 towards the capillary 200 occurs along a primary heat flow direction 204 which is substantially perpendicular to the effective fluid flow direction 206.

However, there is a further—parasitic—heat transfer corresponding to a secondary heat flow direction 208 from the hot liquid close to the fluid outlet interface 212 towards the still colder liquid close to the fluid inlet interface 210. This results in an effective undesired temperature equilibration among different liquid parts or packets, and partially via the thermal coupling body 202, which, in turn, results in an undesired cooling of the liquid close to the fluid outlet interface 212. The parasitic secondary heat flow direction 208 is substantially perpendicular to the primary heat flow direction 204.

According to exemplary embodiments of the invention, it has been surprisingly found that the desired heat transfer along the primary heat flow direction 204 is only slightly reduced, but the parasitic thermal energy flow along the secondary heat flow direction 208 is significantly reduced by a selection of the value of the thermal conductivity of the material of the heat transfer body or thermal coupling body 202 in a range between about 8 W/(m K) and about 100 W/(m K). It has further been surprisingly found that the net pre-heating performance of the liquid by the pre-heater assembly 90 is substantially improved by selecting an only moderately thermally conductive material of the thermal coupling body 202.

The liquid in the capillary 200 flows from the fluid inlet interface 210 to the fluid outlet interface 212 and is heated during its flow by the primary heat flow oriented perpendicular (see reference numeral 204) to its effective fluid flow direction 206. Since the secondary heat flow from the already heated liquid close to the fluid outlet interface 212 back towards the still colder liquid close to the fluid inlet interface 210 occurs, thermal energy flows away from the liquid close to the fluid outlet interface 212 which deteriorates the pre-heating performance of the pre-heater assembly 90. However, in particular if the value of the thermal conductivity of the thermal coupling body 202 is selected as described beforehand, it has turned out that the secondary heat flow reducing the pre-heating performance is significantly weakened and the efficient performance of the pre-heater assembly 90 is improved.

However, it is nevertheless advantageous that the primary heat flow along the primary heat flow direction 204 perpendicular to the effective flow direction 206 is rendered sufficiently efficient, so that the surrounding of the thermal coupling body 202 can be preferably made of a material with a high thermal conductivity such as aluminum. Moreover, it is advantageous that a smallest distance d between the capillary 200 and an exterior surface of the thermal coupling body 202 is sufficiently small to allow for an efficient heat transfer from the heat source 80.

Figures 3, 4, 5, 6, 7:
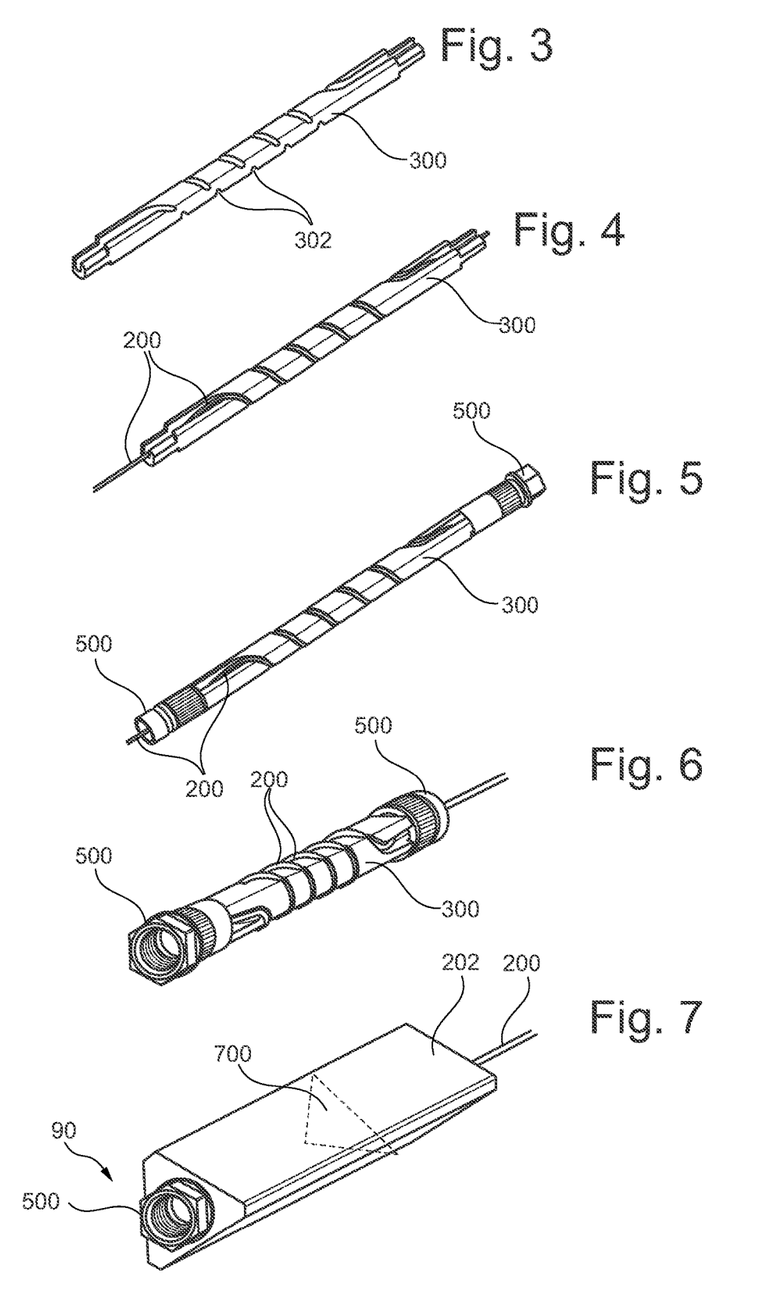
FIG. 3 to FIG. 6 show different three-dimensional views of structures obtained during carrying out a method of manufacturing a pre-heater assembly according to an exemplary embodiment of the invention.
FIG. 7 shows a three-dimensional view of a pre-heater assembly according to an exemplary embodiment of the invention manufactured according to FIG. 3 to FIG. 6.

FIG. 3 to FIG. 6 show different three-dimensional views of structures obtained during carrying out a method of manufacturing a pre-heater assembly 90 according to an exemplary embodiment of the invention, wherein the manufactured pre-heater assembly 90 is shown in FIG. 7.

FIG. 3 shows a carrier 300 which may for instance be made of a material such as plastic or a metal. The carrier 300 is rod-shaped and comprises a circumferentially running groove 302 serving as a guide and an accommodation for a capillary 200 to be wound around the carrier 300.

FIG. 4 shows the carrier 300 with the capillary 200 wound around an exterior surface of the carrier 300. More precisely, the capillary 200 is guided along and accommodated within the groove 302 so as to precisely define the trajectory of the capillary 200 in the pre-heater assembly 90 to be manufactured.

FIG. 5 and FIG. 6 show the arrangement of FIG. 4 with fittings 500 attached to both opposing ends of the carrier 300. These opposing ends are correspondingly shaped to receive the fittings 500 (which are here configured as female fittings). Via the fittings 500, the capillary 200 may be fluidically connected to another fluidic member (such as a fluidic valve, a separating device 30, an injector 40, etc.).

FIG. 7 shows pre-heater assembly 90 according to an exemplary embodiment of the invention which is obtained by overmolding the arrangement of FIG. 5 and FIG. 6 with plastic material to thereby form the thermal coupling body 202. Forming the thermal coupling body 202 from plastic material has the advantage that it can be simply and cheaply manufactured by molding and that a monolithic pre-heater assembly 90 is obtained which promotes a proper thermal coupling to the exterior heat source 80. An exterior surface of the thermal coupling body 202 also constitutes an external surface of the entire pre-heater assembly 90. When viewing the pre-heater assembly 90 from a viewing direction perpendicular to a flange face thereof at which the fittings 500 are located the pre-heater assembly 90 has a substantially V-shape. Thus, the pre-heater assembly 90 is substantially shaped as a regular prism with an equilateral triangular base surface 700.

Figure 8:
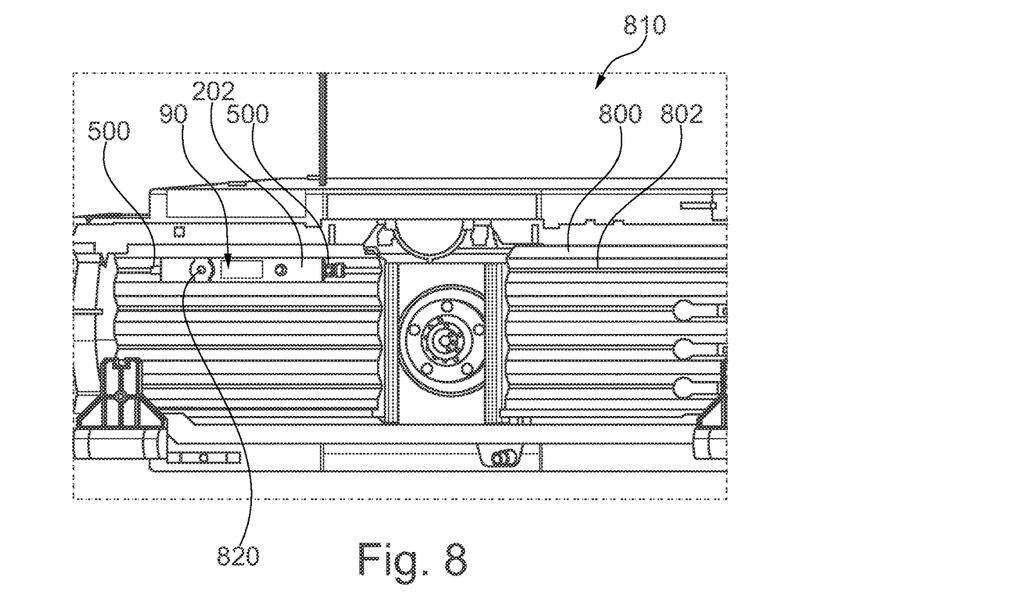
FIG. 8 illustrates a detail of a heating chamber and FIG. 9 illustrates the entire heating chamber of a fluid separation apparatus according to an exemplary embodiment of the invention, wherein the heating chamber is configured for heating a fluid of the fluid separation apparatus and comprises a pre-heater assembly mounted in a recess of a mounting board.
Figure 9:
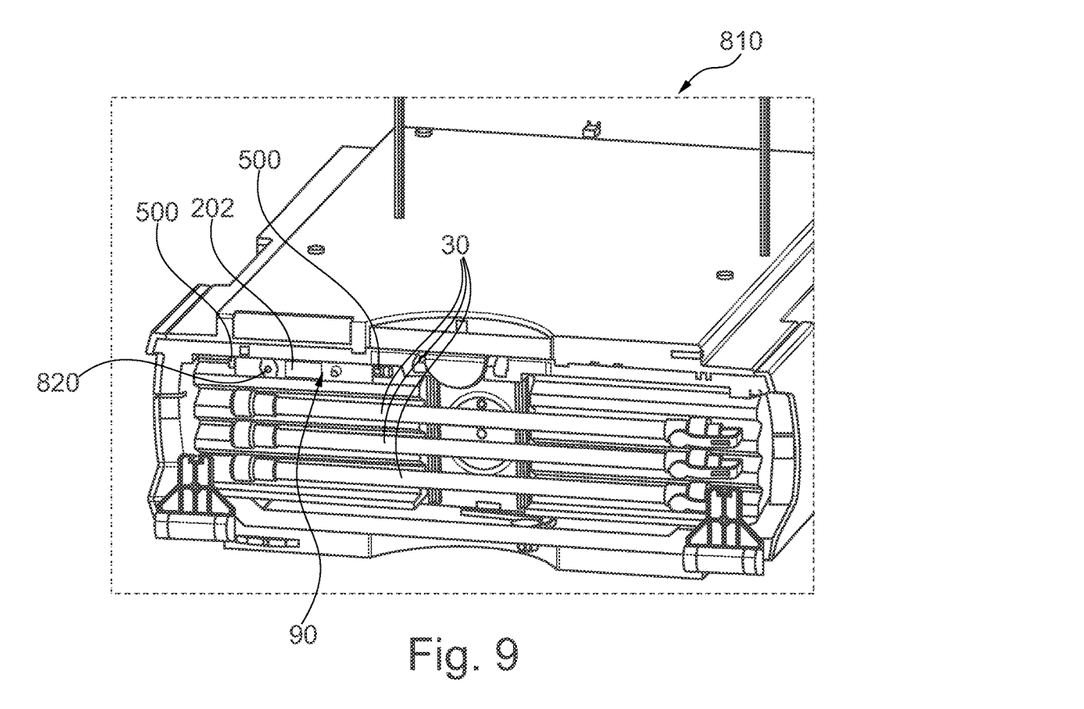

FIG. 8 illustrates a detail of and FIG. 9 illustrates an entire heating chamber 810 of a liquid separation system 10 according to an exemplary embodiment of the invention, wherein the heating chamber 810 is configured for heating a liquid of the liquid separation system 10 and comprises a pre-heater assembly 90 as described referring to FIG. 7 which is mounted in a mounting recess 802 formed as a groove within a mounting board 800 of the heating chamber 810.

The mounting board 800 is a plate made of a highly thermally conductive material such as aluminum. A plurality of substantially V-shaped grooves are formed as the mounting recesses 802 in the mounting board 800. The mounting recesses 802 are arranged horizontally and in parallel to one another. At the back side of the mounting board 800 (not shown) heat source 80 may be mounted for heating the mounting board 800. By heat conduction, the pre-heater assembly 90 as shown in FIG. 7 and being mounted with full-face contact within one of the mounting recesses 802 is heated by the heated mounting board 800. Due to the modular arrangement of the mounting recesses 802, a plurality of pre-heater assemblies 90 and/or other fluidic members (such as one or more separation devices 30) may be mounted on the mounting board 800 and hence in the heat chamber 810.

In FIG. 8, only one pre-heater assembly 90 is mounted in one of the mounting recesses 802. The pre-heater assembly 90 shown in FIG. 7 is simply placed in one of the mounting recesses 802, and subsequently a turning knob 820 (as an example for a pre-heater fastening element) is turned (for instance by 90°) so that its radially outermost portion engages an undercut section (for instance shaped as a dovetail groove) in a surface portion of the mounting recess 802 and thereby fastens the pre-heater assembly 90 in the mounting recess 802. The corresponding V-shapes of the pre-heater assembly 90 and of the mounting recess 802 substantially simplify the mounting procedure by providing guidance and by also promoting a proper heat transfer by heat conduction.

As can be taken from FIG. 9, additionally three separation devices 30 (here configured as chromatographic separation columns) are mounted in other mounting recesses 802. The separation devices 30 are mounted on the respective mounting recess 802 with a gap or some distance between an innermost surface of the mounting recess 802 so that the separation devices 30 are heated by heat convection rather than by heat conduction, which may be desired for separation devices 30 to obtain a homogeneous heating.

Figure 10:
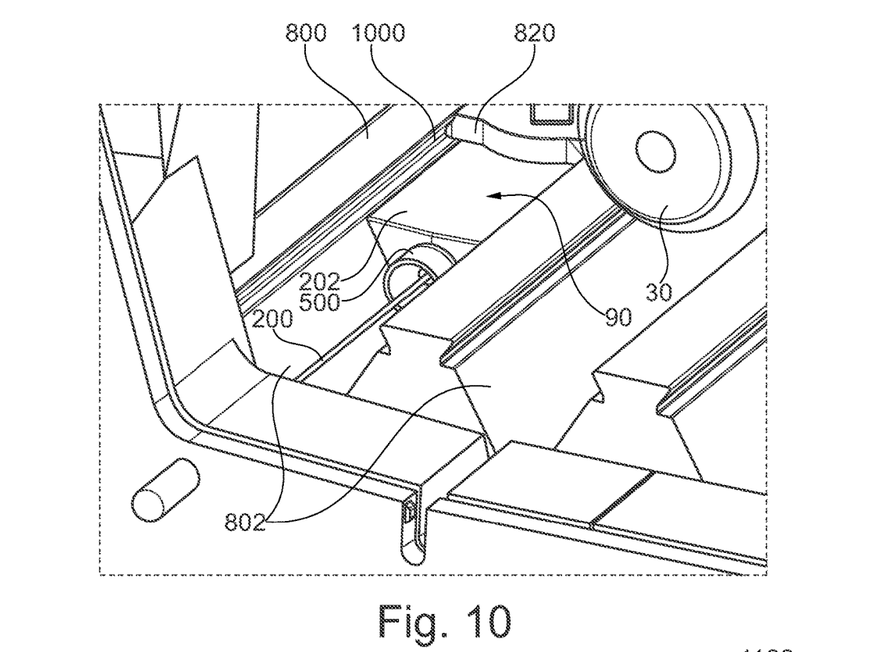
FIG. 10 shows a three-dimensional view of a portion of a pre-heater assembly according to an exemplary embodiment of the invention mounted in a recess of a mounting board of a fluid separation apparatus according to an exemplary embodiment of the invention.

FIG. 10 shows a three-dimensional view of a portion of pre-heater assembly 90 mounted in a corresponding mounting recess 802 of mounting board 800. FIG. 10 particularly shows as to how the turning knob 820 engages into undercut section 1000 to provide for a reversible fastening. The pre-heater assembly 90 rests with a form closure within the correspondingly shaped mounting recess 802.

Figure 11:
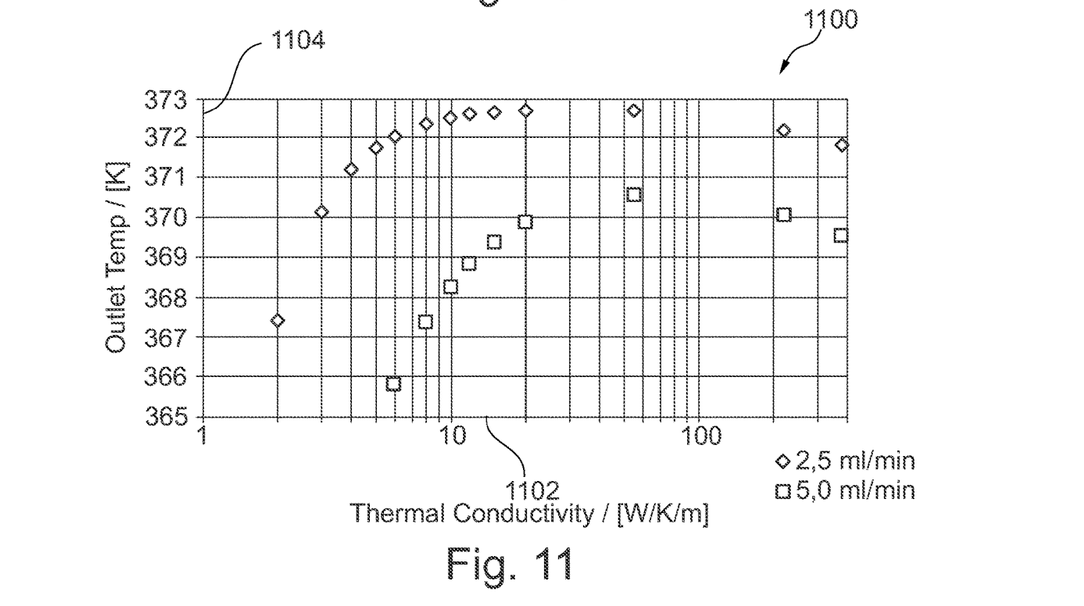
FIG. 11 is a diagram illustrating a dependency of an outlet temperature of fluid conducted through a pre-heater assembly as a function of the thermal conductivity of a thermal coupling body of a pre-heater assembly according to an exemplary embodiment.

FIG. 11 is a diagram 1100 illustrating a dependency of an outlet temperature (plotted along an ordinate 1104) of liquid conducted through a pre-heater assembly 90 as a function of the thermal conductivity (plotted along an abscissa 1102) of a thermal coupling body 202 of the pre-heater assembly 90 according to an exemplary embodiment. This information is displayed in FIG. 11 for two different flow rates of 2.5 ml/min and 5.0 ml/min.

The results in FIG. 11 are the result of a simulation. The outlet temperature of the liquid at the fluid outlet interface 212 is determined by a simulation for different materials of the thermal coupling body 202. It can be taken from FIG. 11 that approximately in a range from 8 W/(m K) to 100 W/(m K) better results can be obtained as with the conventional used and significantly more expensive and cumbersome materials aluminum and copper.

It should be noted that the term "comprising" does not exclude other elements or features and the term "a" or "an" does not exclude a plurality. Also elements described association with different embodiments may be combined. It should also be noted that reference signs in the claims shall not be construed as limiting the scope of the claims.

The invention claimed is:

1. A fluid separation apparatus for separating a fluidic sample into a plurality of fractions, the apparatus comprising:
   a fluid drive unit configured for driving a fluid comprising a mobile phase and the fluidic sample in the mobile phase;
   a separation unit configured for separating the fluidic sample into the plurality of fractions;
   a heat source;
   a board thermally coupled with the heat source, and comprising at least one accommodation recess; and
   a pre-heater assembly mounted in the at least one accommodation recess, and configured for pre-heating the fluid prior to supply of the fluid to the separation unit, wherein the pre-heater assembly comprises:
      a capillary having a lumen and being configured for conducting the fluid; and
      a thermal coupling body contacting at least part of the capillary, having a value of thermal conductivity in a range between 8 W/(m K) and 100 W/(m K), and being arrangable so that heat generated by the heat source is supplied to the capillary via at least part of the thermal coupling body;
   wherein the thermal coupling body is made of one selected from the group consisting of: a plastic molding compound, a plastic filled with thermally conductive particles, and a plastic composition.

2. The fluid separation apparatus claim 1, wherein the heat source is configured for generating heat for heating the separation unit.

3. The fluid separation apparatus of claim 1, comprising an injector for injecting the fluidic sample into the mobile phase, wherein the injector is arranged upstream of the pre-heater assembly in a flow direction of the fluid.

4. The fluid separation apparatus of claim 1, wherein the board comprises a material selected from the group consisting of: a material having a thermal conductivity of at least 200 W/(m K); aluminium; and copper.

5. The fluid separation apparatus of claim 1, further comprising at least one of:
- a detector configured to detect separated fractions of the fluidic sample;
- a fractioner unit configured to collect separated fractions of the fluidic sample;
- a data processing unit coupled to at least the detector of the fluid separation apparatus; and
- a degassing apparatus for degassing at least part of the fluid.

* * * * *